United States Patent
Conti Vecchi

(10) Patent No.: US 7,340,980 B2
(45) Date of Patent: Mar. 11, 2008

(54) TATTOO MACHINE

(76) Inventor: Luigi Conti Vecchi, Via Crespellani, 72, 41100 Modena (IT)

( * ) Notice: Subject to any disclaimer, the term of this patent is extended or adjusted under 35 U.S.C. 154(b) by 113 days.

(21) Appl. No.: 11/195,629

(22) Filed: Aug. 3, 2005

(65) Prior Publication Data

US 2007/0028722 A1    Feb. 8, 2007

(51) Int. Cl.
*B43K 5/00* (2006.01)
*A61B 17/35* (2006.01)

(52) U.S. Cl. ........................ 81/9.22; 606/186

(58) Field of Classification Search ............... 81/9.22; 606/116, 186, 185; 30/362, 366; D24/146; 74/89.2, 500.5, 502.2, 502.6; 173/171, 147, 173/151; 464/88, 173, 52, 53
See application file for complete search history.

(56) References Cited

U.S. PATENT DOCUMENTS

| | | | | |
|---|---|---|---|---|
| 1,555,647 A | * | 9/1925 | Falconer | 192/82 R |
| 3,461,687 A | * | 8/1969 | Siegal | 464/52 |
| 3,611,748 A | * | 10/1971 | Wallgren | 464/52 |
| 4,031,783 A | * | 6/1977 | Paul et al. | 81/9.22 |
| 4,796,624 A | | 1/1989 | Trott et al. | |
| 5,551,319 A | * | 9/1996 | Spaulding et al. | 81/9.22 |
| 6,270,087 B1 | * | 8/2001 | Mickel et al. | 279/75 |
| 6,345,553 B1 | * | 2/2002 | Adler et al. | 81/9.22 |
| 6,814,157 B2 | * | 11/2004 | Maras | 173/171 |

FOREIGN PATENT DOCUMENTS

| | | |
|---|---|---|
| DE | 43 02 096 A1 | 7/1994 |
| DE | 198 36 376 A1 | 2/2000 |
| DE | 19836376 A1 * | 2/2000 |
| DE | 200 12 369 | 12/2000 |
| WO | WO 01/58515 A | 8/2001 |

\* cited by examiner

*Primary Examiner*—Joseph J. Hail, III
*Assistant Examiner*—Bryan Muller
(74) *Attorney, Agent, or Firm*—Browdy and Neimark, PLLC

(57) ABSTRACT

A tattoo machine, comprising at least one elongated hollow body inside which there is a cavity for containing a coloring liquid that is connected to the outside by a hole provided at one end of the hollow body, a needle that can slide in a reciprocating fashion along the hole, and elements for moving the needle between a first end position, in which the needle protrudes at least partially from the hollow body, and a second end position, in which the needle is completely accommodated within the hollow body, the movement elements comprising a motor that can be associated with the needle by interposing motion transmission elements provided with a flexible cable, a first end of which can be associated with the motor and a second end of which can be associated with the needle.

12 Claims, 4 Drawing Sheets

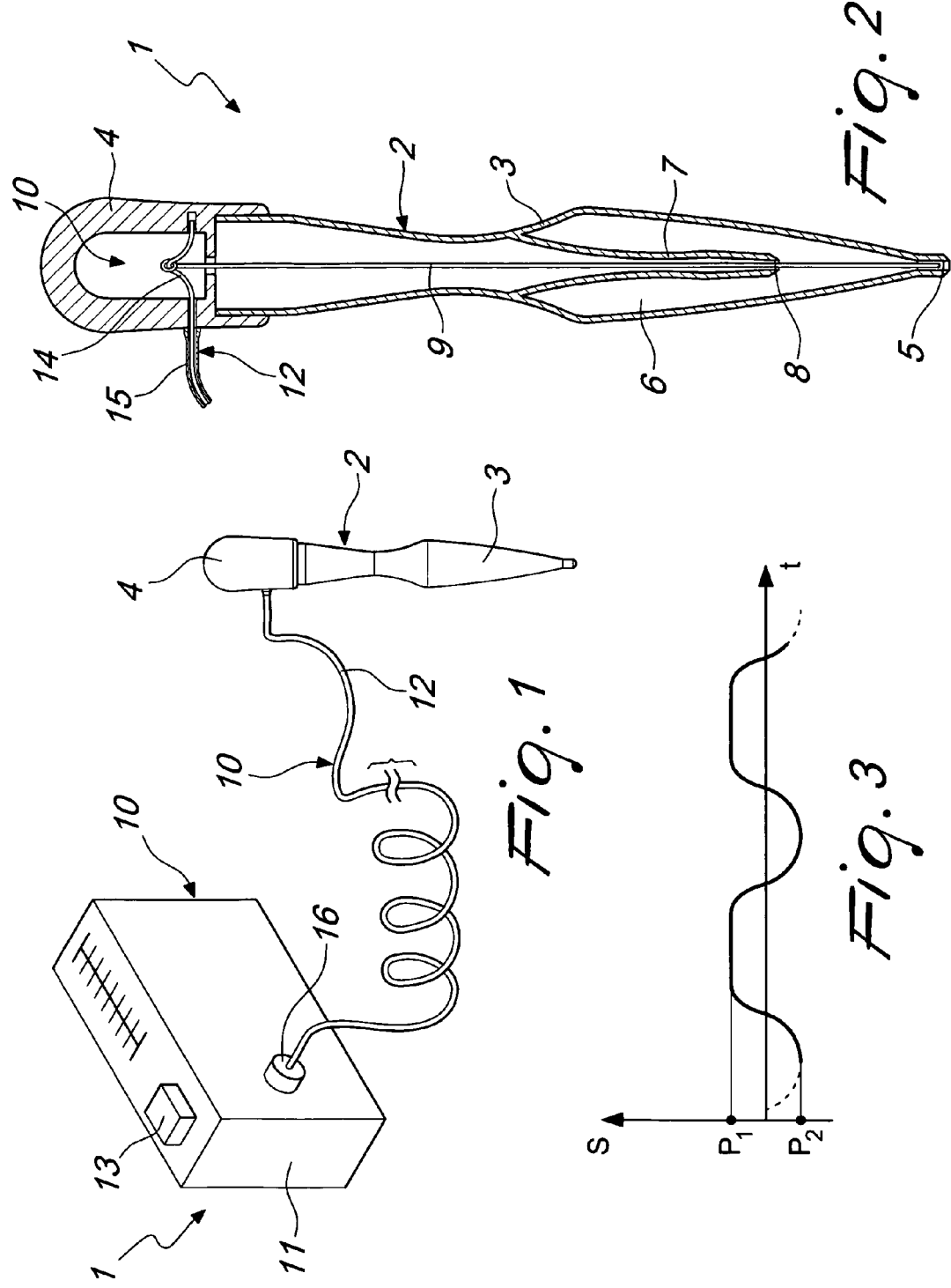

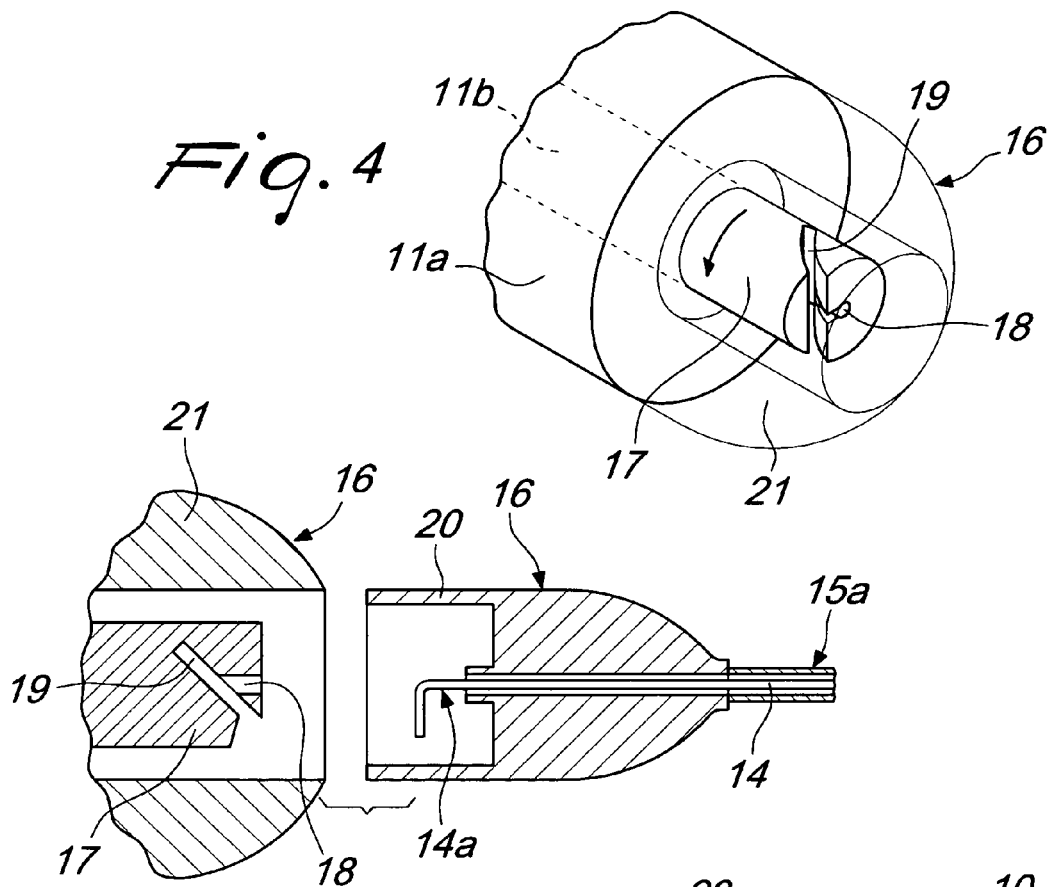
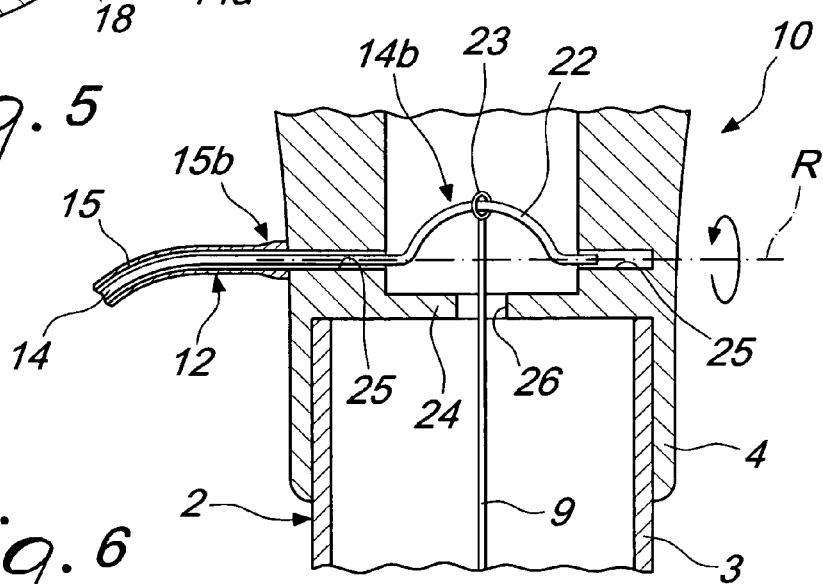

TATTOO MACHINE

BACKGROUND OF THE INVENTION

Tattooing is a widespread and widely practiced body decoration technique, in which markings, drawings, letters, symbols or other patterns are etched onto the body by piercing the permanent layer of the skin and simultaneously injecting colored pigments.

In recent years, this technique has been used widely in the aesthetic and cosmetic field in the form of so-called "permanent makeup", which consists in tattooing the parts of the face (eyebrows, eye line, lips . . . ) that are normally made up with traditional cosmetic products.

To perform this technique, it is known to use devices commonly conventionally known as tattoo machines, which have an elongated hollow body that can be maneuvered manually and is suitable to contain a coloring liquid and to act as a guide for one or more movable needles.

Commonly, one end of the hollow body is provided with an exit hole for the liquid, inside which the needle can slide in a reciprocating fashion between two end positions, i.e., a position in which it is fully inserted within the hollow body and a position in which the tip of the needle protrudes from the hole in order to penetrate the skin and entrain the coloring liquid with it.

Motor means are generally fitted on the hollow body and push the needle between the two end positions, imparting thereto a vibrating motion, i.e., with sudden and immediate changes in direction; in practice, when the end position that lies outside the hollow body is reached, the tip of the needle is immediately retracted up to the opposite end position, where it reverses again suddenly.

The motor means are activated not only to allow the needle to penetrate the skin while making the tattoo but also to fill the hollow body with the required coloring liquid; the hole for the exit of the liquid from the hollow body is in fact commonly used also as an inlet, and filling is performed generally by capillary action by dipping the end of the hollow body provided with the hole in a container that contains the pigment and by moving the needle in order to facilitate its drawing.

These known tattoo machines are not free from drawbacks, including the fact that the motor means with which they are provided have substantial dimensions and increase considerably the weight of the hollow body, accordingly limiting its maneuverability and easy handling.

Moreover, the vibrating motion to which the needle is subjected does not allow the coloring liquid to spread within the skin uniformly, since the pigment does not have the time to be absorbed by the epidermis when the tip of the needle reaches the end position that lies outside the hollow body.

In this regard, it is noted that in order to improve the diffusion of the color within the skin, the operator is often forced to apply more pressure to the tattoo machine and to incline it, increasing the penetration of the needle and accordingly the pain of the person on which the tattoo is produced, in addition to causing incorrect healing of the skin.

Moreover, the needles used in conventional tattoo machines are often substantially rigid and thick and even slight pressures on the hollow body can cause excesses in skin piercing.

Moreover, it is noted that for health and sanitary reasons the needles must be strictly sterilized after each use or must be of the disposable type; in both cases they require repetitive steps for fitting/removing in/from the hollow body, requiring considerable time and particular care on the part of the operator.

In particular, the fitting step is particularly delicate, since the needles must not be contaminated at all in order to avoid compromising the health of the person with whom they must make contact.

Finally, it is noted that known tattoo machines can contain very limited amounts of coloring liquid inside them, since the higher the level reached by the liquid within the hollow body, the larger the amount of pigment that adheres to the needle and is entrained with it during its outward motion and therefore contrasts the drawing action; in practice, this forces the user to perform repeated filling operations, slowing the execution of the tattoo considerably.

SUMMARY OF THE INVENTION

The aim of the present invention is to eliminate the above-mentioned drawbacks of the background art, by providing a tattoo machine that is light and compact, allows to improve the diffusion of the coloring liquid in the skin, simplifies the tasks of the operator, reduces the pain caused by the piercing action and increases its safety for the person who undergoes it, particularly avoiding the formation of cheloids caused by poor healing.

Within this aim, an object of the present invention is to provide a tattoo machine that is simple, relatively easy to provide in practice, safe in use, effective in operation, and has a relatively low cost.

This aim and this and other objects that will become better apparent hereinafter are achieved by the present tattoo machine, comprising at least one elongated hollow body inside which there is a cavity for containing a coloring liquid that is connected to the outside by means of a hole provided at one end of said hollow body, at least one needle that can slide in a reciprocating fashion along said hole, and means for moving said needle between a first end position, in which the needle protrudes at least partially from said hollow body, and a second end position, in which the needle is completely accommodated within said hollow body, characterized in that said movement means comprise motor means that can be associated with said needle by interposing motion transmission means that are provided with at least one flexible cable, a first end of which is associated with said motor means and a second end of which is associated with said needle.

BRIEF DESCRIPTION OF THE DRAWINGS

Further characteristics and advantages of the present invention will become better apparent from the following detailed description of a preferred but not exclusive embodiment of a tattoo machine, illustrated by way of non-limiting example in the accompanying drawings, wearing:

FIG. 1 is a perspective view of the tattoo machine according to the invention;

FIG. 2 is a sectional view of the hollow body of the tattoo machine according to the invention;

FIG. 3 plots a possible rule of motion of the needle of the tattoo machine according to the invention;

FIG. 4 is a perspective view, shown partially in phantom lines, of the quick coupling means of the tattoo machine according to the invention;

FIG. 5 is a sectional view of the quick coupling means of the tattoo machine according to the invention;

FIG. 6 is a sectional view of a first embodiment of the movement means of the tattoo machine according to the invention, with the needle in the second end position;

DESCRIPTION OF THE PREFERRED EMBODIMENTS

Figure 7:
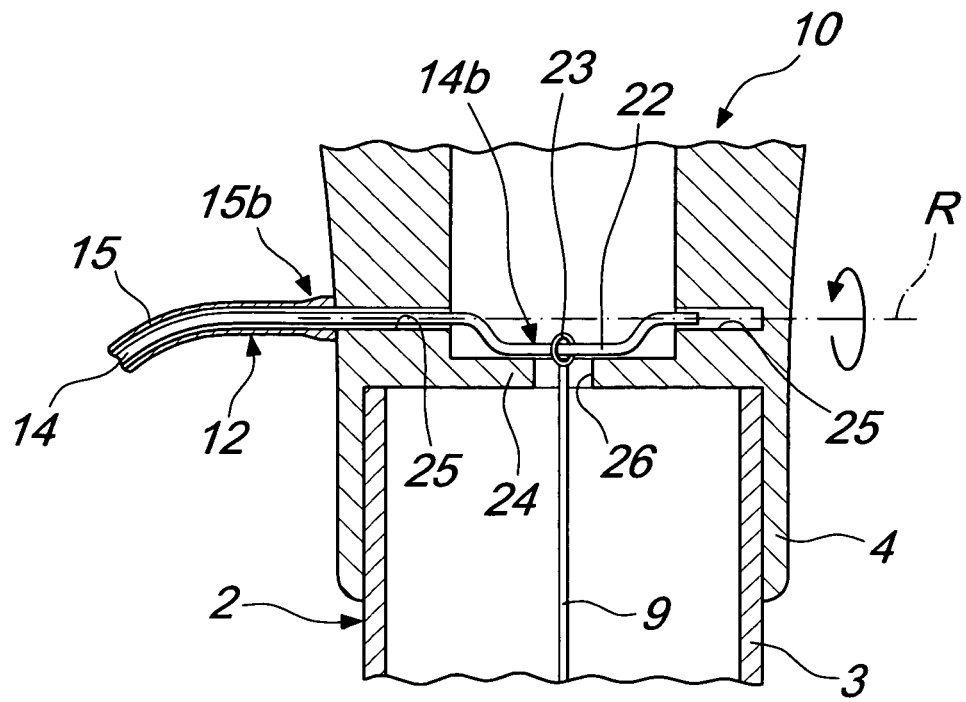
FIG. 7 is a sectional view of the movement means of FIG. 6, with the needle in the first end position.

With reference to the figures, the reference numeral 1 generally designates a tattoo machine.

The tattoo machine 1 comprises an elongated hollow body 2, which is formed by a tubular segment 3, in which one end is closed with a cap 4, a hole 5 being formed at the opposite end.

The body 2 is suitable to be maneuvered manually by an operator; the lateral surface of the tubular segment 3, in particular, has a recessed profile at the substantially central part, so as to be particularly anatomically contoured and easy to handle.

A cavity 6 for containing a coloring liquid is formed within the hollow body 2 and is connected to the outside by means of the hole 5.

In particular, the cavity is delimited between the walls of the tubular segment 3 and an internal wall 7, which is substantially conical and extends from such segment so that the concavity is directed away from the hole 5.

A hole 8 that is coaxial to the hole 5 is provided at the pointed end of the wall.

The tattoo machine 1 is provided with a needle 9, which crosses the cavity 6 from side to side and is inserted, so that it can slide with a reciprocating motion, within the hole 5 and the hole 8; in particular, the transverse dimensions of the needle 9 and of the hole 8 are mutually complementary, so as to keep substantially in contact during the sliding of the needle and prevent the passage of coloring liquid through said hole.

The needle 9 is particularly fine and substantially flexible; its dimensions and rigidity are set so that during penetration in the skin it can flex in order to avoid piercing the skin excessively.

In the particular embodiment of the present invention shown in the figures, the needle 9 is a single needle, but alternative embodiments in which the tattoo machine 1 has a plurality of mutually parallel needles are not excluded.

Further, the present invention is provided with means 10 for moving the needle 9 between a first end position, in which the needle protrudes at least partially from the hollow body 2 through the hole 5, and a second end position, in which the needle is accommodated completely in the hollow body.

The movements means 10 comprise motor means 11, which are external to the hollow body 2 and can be connected to the needle 9 by interposing motion transmission means 12.

In particular, the motor means 11 comprise a fixed portion 11a and a movable portion 11b that has a rotary motion.

The rotation rate of the movable portion 11b can be selected by the user by way of adjustment means 13, which for example can comprise a pedal, a lever, a button or the like.

According to the invention, the transmission means 12 include a flexible cable 14, in which a first end 14a can be associated with the movable portion 11b and a second end 14b, arranged opposite the first end, is connected to the needle 9.

The flexible cable can rotate about itself, sliding rotationally within a corresponding flexible tube 15, in which a first end 15a can be associated with the fixed portion 11a and a second end 15b, arranged opposite the first end, is fixed to the external surface of the cap 4, for example by adhesive bonding.

The cable 14 is substantially longer than the tube 15, and its ends 14a and 14b protrude from the ends 15a and 15b of the tube.

The portions 11a and 11b of the motor means 11 are provided with means 16 for the quick coupling of the transmission means 12.

The coupling means comprise a cylindrical element 17, which can rotate about its own axis together with the movable portion 11b; such element is provided with an axial slot 18 and with a notch 19 that is oblique with respect to the slot.

The first end 14a of the cable 14 is bent at right angles in order to be inserted in the slot so that the bent part is engaged within the notch 19.

Further, the tube 15 can be associated with the motor means 11 by way of a substantially tubular portion 20, which has a circular cross-section, is connected to the first end of the tube 15, and can be inserted in a corresponding hub 21 provided on the fixed portion 11a coaxially to the element 17.

Insertion of the portion 20 in the hub 21 provides a detachable fixing produced by friction between the cylindrical surfaces in mutual contact.

It should be noted that the insertion of the portion 20 in the hub 21 allows to arrange the first end 14a of the cable 14 in contact with the element 17, proximate to the slot 18; regardless of the relative position assumed by the bent part of the cable 14 with respect to the notch 19, the rotation of the element 17 upon activation of the motor means 11 is such as to capture the bent part within the notch 19 and rotationally entrain the cable 14.

The second end 14b of the cable 14 ends inside the hollow body 2, where it is supported so that it can rotate about a rotation axis R, which is substantially transverse with respect to the needle 9; moreover, the end is associated with eccentric means that are suitable to convert the rotary motion of the cable 14 into the reciprocating rectilinear motion of the needle 9.

Advantageously, the eccentric means are formed by a bent portion 22 of the second end 14b of the cable 14 in which a ring 23 associated with the needle 9 is inserted snugly, so that the rotation of the cable 14 is such as to entrain said needle so that it moves between the two end positions.

Further, the movement means 10 comprise means 24 for temporarily stopping the needle 9 in the first end position.

In practice, the movement means 10 are such as to impart to the needle 9 a motion for example of the type described by the chart shown in FIG. 3, wherein the ordinates plot the space S covered by the needle 9 between the first end position $P_1$ and the second end position $P_2$, while the abscissas plot the time t.

In a first embodiment of the movement means 10 shown in FIGS. 6 and 7, the bent portion 22 substantially forms a circular arc, the ends of which are rotationally rigidly coupled in two eyes 25, which are aligned along a direction that is substantially perpendicular to the needle 9; such direction defines the rotation axis R.

In this embodiment, the stop means 24 are constituted by a barrier body, which is arranged along the path of the bent portion 22, between such portion and the hole 5, and is suitable to cause the elastic deformation of the bent portion 22 in order to reduce the distance of the ring 23 from the rotation axis R.

In particular, the barrier body 24 is a type of partition that lies transversely to the needle 9 and in which there is a central opening 26, in which the needle is arranged so as to pass through it.

The operation of the stop means 24 is as follows: during the rotation of the cable 14 about the rotation axis R, the bent portion 22 is forced to make contact with the barrier body 24 and to undergo deformation by utilizing its flexibility and then recovers its original shape after it has moved beyond the body.

In this deformation, the bent portion 22 is compressed against the barrier body and the distance of the ring 23 from the rotation axis R decreases considerably; as long as the bent portion 22 remains deformed, further advancements of the needle 9 in the direction for exiting from the hole 5 are not possible, in practice keeping said needle in the first end position.

Figure 8:
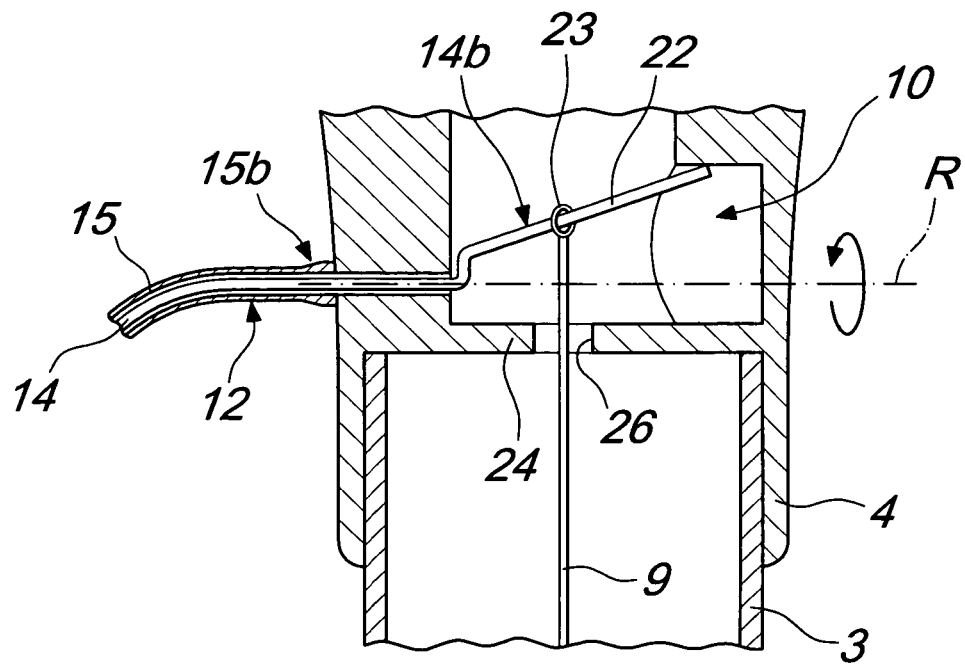
FIG. 8 is a sectional view of a second embodiment of the movement means of the tattoo machine according to the invention, with the needle in the second end position.
Figure 9:
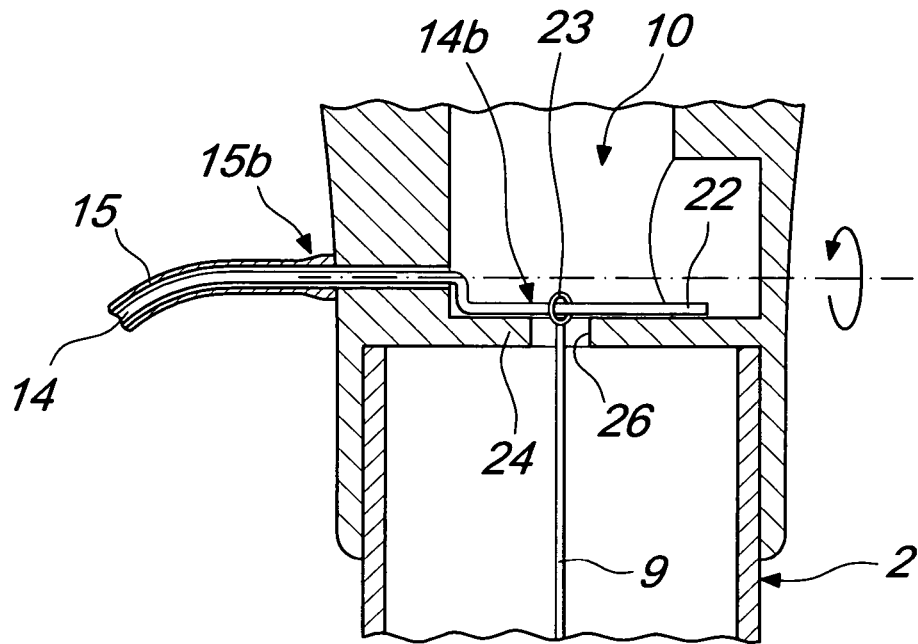
FIG. 9 is a sectional view of the movement means of FIG. 8, with the needle in the first end position.

In a second embodiment of the movement means 10, shown in FIGS. 8 and 9, the bent portion 22 forms a straight segment that is substantially inclined with respect to the rotation axis R and in particular is arranged at right angles with respect to the needle 9.

In such second embodiment, the stop means 24 are of a kind that is similar to the stop means of the first embodiment illustrated earlier and likewise reproduce their operation.

Figure 10:
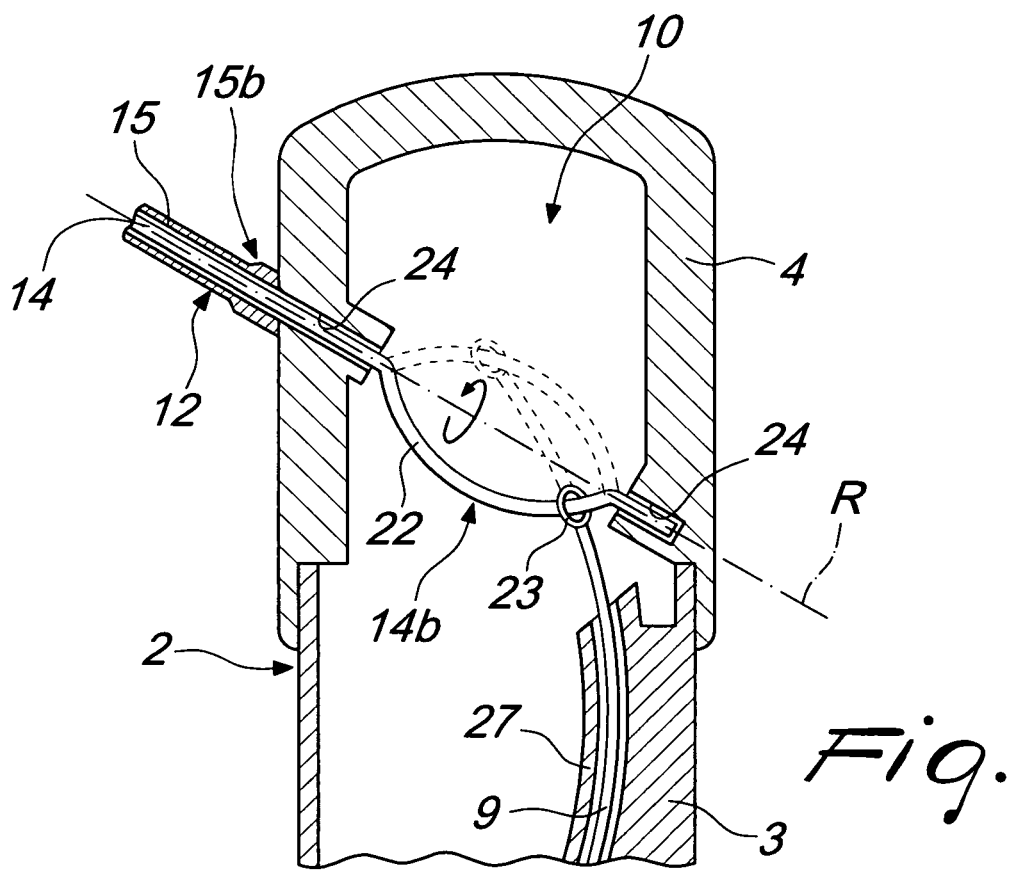
FIG. 10 is a sectional view of a third embodiment of the movement means of the tattoo machine according to the invention.

In a third embodiment of the movement means 10, shown in FIG. 10, the bent portion 22 forms a circular arc that is similar to the circular arc related to said first embodiment.

The stop means 24 are instead constituted by two slots, which are formed in the cap 4 and, like the eyes 25, define the rotation axis R of the cable 14 but, differently from said eyes, are aligned along a direction this is substantially oblique with respect to the needle 9.

Further, the needle 9 is inserted so that it can slide within a guiding duct 27, which is associated with the tubular segment 3 and is suitable to limit its flexing.

In particular, the ring 23 can slide on the bent portion 22 between a first configuration, in which it is arranged proximate to the rotation axis R, at the first end position of the needle 9, and a second configuration, in which it is spaced from the axis, at the second end position, in FIG. 10, the first configuration is shown in solid lines and the second configuration is shown in dashed lines.

In this third embodiment, the operation of the stop means 24 is as follows: during the rotation of the cable 14, the ring 23 is made to slide along the bent portion 22, pushing the needle 9 between the two end positions.

Owing to the particular relative inclination between the rotation axis R and the needle 9, moreover, the ring 23 periodically varies its distance from the axis; in particular, it is very close to the rotation axis R when the needle 9 is exiting from the hole 5, so that during the rotation of the bent portion 22 the needle substantially does not move with respect to the first end portion.

All the embodiments of the tattoo machine 1 described above and illustrated in the figures are provided with motor means 11 that have a rotating movable portion 11b; however, alternative embodiments of the present invention are not excluded in which the movable portion 11b has a reciprocating rectilinear motion that can be transmitted to the needle 9 by means of a cable 14 that can slide longitudinally within the tube 15.

In this alternative embodiment, the cable 14 can be rigidly connected to one end of the needle 9 in order to move it; moreover, advantageously, it is possible to provide elastic means that act on the needle 9 for its passage from the second end position to the first end position and yield to the return action of the cable 14 for the reverse passage of the needle 9 from the first end position to the second end position.

In practice, the presence of the elastic means allows to keep the cable 14 constantly in traction, both during the exit and during the retraction of the needle from/into the hollow body 2.

In practice it has been found that the described invention achieves the intended aim and object.

In this regard, it is noted that the particular solution of using motor means that are external to the hollow body allows to reduce the weight of the tattoo machine that is handled by the operator, making it considerably maneuverable and easy to use.

The present tattoo machine, further, allows to stop the needle in the first end position for a time that is sufficient to allow the coloring liquid to spread within the skin and be absorbed by the epidermis.

Moreover, it is noted that the particular flexibility of the cable, as well as the flexibility of the needle, allow to avoid any skin piercing excesses; the cable and the needle are in fact both capable of bending in case of given resistances opposed by the skin, preventing the tip of the needle from reaching depths that are particularly painful or can cause incorrect healing.

Moreover, it is stressed that the present invention can be filled with considerably larger quantities of coloring liquid than known types of tattoo machine; this is due to the fact that the amount of pigment that adheres to the needle during filling is particularly limited and at the most is proportional to the distance between the hole formed in the hollow body and the hole formed in the internal wall that delimits the cavity.

Finally, the present invention is particularly suitable for single-use applications; the hollow body that contains one or more needles can in fact be distributed together with the cable and the flexible tube within sterilized packages, conveniently separated from the motor means, to which it can be connected easily by way of the quick coupling means, without forcing the operator to perform demanding operations for fitting/removing the needle/needles on/from the hollow body.

The invention thus conceived is susceptible of numerous modifications and variations, all of which are within the scope of the appended claims.

All the details may further be replaced with other technically equivalent elements.

In practice, the materials used, as well as the contingent shapes and dimensions, may be any according to requirements without thereby abandoning the scope of the protection of the appended claims.

What is claimed is:

1. A tattoo machine, comprising at least one elongated hollow body inside which there is a cavity for containing a coloring liquid that is connected to the outside by a hole provided at one end of said cavity, at least one needle that can slide in a reciprocating fashion along said hole, and a moving mechanism which moves said needle between a first end position, in which the needle protrudes at least partially from said hollow body, and a second end position, in which the needle is completely accommodated within said hollow body, wherein said moving mechanism comprises a motor that can be associated with said needle by interposing a motion transmission apparatus having at least one flexible cable, a first end of which is associated with said motor and a second end of which is associated with said needle;

wherein said second end of the cable is arranged within said hollow body so that it can rotate about a rotation axis that lies substantially transversely to said needle and is associated with an eccentric element for converting rotary motion of said cable into reciprocating rectilinear motion of said needle; and wherein said moving mechanism comprises means for temporarily stopping said needle in said first end position.

2. The tattoo machine of claim 1, wherein said transmission apparatus further comprises at least one flexible tube, in which a first end can be associated with said motor and a second end can be associated with said hollow body, said cable being arranged inside said tube so that said cable can slide.

3. The tattoo machine of claim 2, wherein said cable is substantially longer than said tube, said cable ends respectively protruding from said tube ends.

4. The tattoo machine of claim 1, wherein said motor is external to said hollow body.

5. The tattoo machine of claim 2, wherein said motor comprises at least one movable portion and at least on fixed portion, which are provided with means for quick coupling of said transmission apparatus.

6. The tattoo machine of claim 5, wherein said motor comprises adjustment means for adjusting the speed of said movable portion.

7. The tattoo machine of claim 6, wherein said adjustment means comprise a pedal, or lever, or a button.

8. The tattoo machine of claim 1, wherein said eccentric element are formed by a folded portion in said second end of the cable in which a ring is inserted snugly, said ring being engaged with said needle, the rotation of said cable being suitable to move said needle between said first and second end positions.

9. The tattoo machine of claim 8, wherein said means for temporarily stopping said needle comprise at least one barrier body, which is arranged along a path of said bent portion on the second end of the cable, located between said bent portion and said hole, and is suitable to produce elastic deformation of said bent portion in order to reduce the distance of said ring from said rotation axis at said first end position of said needle.

10. The tattoo machine of claim 1, wherein said cavity is delimited between external walls of said hollow body and at least one internal substantially conical wall, which extends from said hollow body so that the concavity of said conical wall is directed away from said hole and in which there is at least one additional hole in which said needle is inserted so that it can slide.

11. The tattoo machine of claim 10, wherein transverse dimensions of said needle and of said additional hole are substantially mutually complementary to prevent passage of the coloring liquid from said cavity into said hollow body.

12. The tattoo machine of claim 1, wherein said needle is substantially flexible.

* * * * *